(12) United States Patent
Putnam

(10) Patent No.: US 6,944,638 B1
(45) Date of Patent: Sep. 13, 2005

(54) MEDICATION DOSAGE CALCULATOR

(76) Inventor: Katharine T. Putnam, 3860 NW. 35th Pl., Gainesville, FL (US) 32606

( * ) Notice: Subject to any disclaimer, the term of this patent is extended or adjusted under 35 U.S.C. 154(b) by 645 days.

(21) Appl. No.: 09/992,793

(22) Filed: Nov. 14, 2001

(51) Int. Cl.[7] .......................................... G06F 19/00
(52) U.S. Cl. ..................... 708/206; 708/132
(58) Field of Search ............... 708/132, 134, 708/206

(56) References Cited

U.S. PATENT DOCUMENTS

| | | | |
|---|---|---|---|
| 4,709,331 A * | 11/1987 | Barkett et al. ............ 708/130 |
| 4,714,462 A | 12/1987 | DiDomenico |
| 4,807,170 A | 2/1989 | Kulli et al. |
| 4,810,243 A | 3/1989 | Howson |
| 4,898,578 A | 2/1990 | Rubalcaba, Jr. |
| 5,088,981 A | 2/1992 | Howson et al. |
| 5,101,368 A * | 3/1992 | Kaplan ....................... 708/206 |
| 5,261,702 A | 11/1993 | Mayfield |
| 5,272,318 A | 12/1993 | Gorman |
| 5,630,664 A | 5/1997 | Farrelly |
| 5,681,285 A | 10/1997 | Ford et al. |
| 5,772,635 A | 6/1998 | Dastur et al. |
| 5,781,442 A | 7/1998 | Engleson et al. |
| 5,915,971 A | 6/1999 | Ramsay et al. |
| 6,167,412 A | 12/2000 | Simons |
| 6,188,570 B1 * | 2/2001 | Borkowski ................. 361/683 |
| 6,273,727 B1 * | 8/2001 | Ramsay et al. ............ 434/262 |
| 2004/0143346 A1 * | 7/2004 | Francis et al. ................ 700/1 |

* cited by examiner

*Primary Examiner*—D. H. Malzahn
(74) *Attorney, Agent, or Firm*—Saliwanchik, Lloyd & Saliwanchik

(57) ABSTRACT

The subject invention provides a system and method for quick and easy calculation of medication dosages to overcome problems in current methods and systems for calculating dosages. The invention can be implemented in numerous ways, including as a system, a device, a method, or a computer readable medium. Specifically exemplified herein are embodiments for use in the healthcare industry.

27 Claims, 3 Drawing Sheets

MEDICATION DOSAGE CALCULATOR

FIELD OF THE INVENTION

The present invention relates to devices and methods for performing medical calculations. In particular, the present invention relates to convenient devices and methods providing simple, immediate, and reliable conversion of medication dosages for administering prescribed medications to a patient/client.

BACKGROUND OF THE INVENTION

To effectively assist in the treatment of patients, healthcare professionals (nurses, medical assistants, paramedics, etc.) are responsible for performing accurate calculations and measurements of medications prescribed by medical physicians. Generally, the various units of doctor-prescribed medication are different from the units of medication defined by a pharmacy. Clinical staff must therefore appropriately convert and precisely calculate a medication dosage in accordance with both the physician's order and pharmaceutical standards. Due to the stressful environment associated with emergency situations as well as the long and difficult hours typically required in the healthcare profession, verification of manual dosage calculations has been very difficult or non-existent even though such verification has long been desirable.

Without proper verification, miscalculations in dosages will occur. According to a November 1999 report from the Institute of Medicine, clinical mistakes in calculating medical dosage, among other factors, kill an estimated 44,000 to 98,000 hospitalized Americans each year. Another article reports that "calculation errors in prescribing are a well-recognized problem, in which errors in decimal point placement, mathematical calculation, or expression of dosage regimen account for 59.5% of dosage errors. Conclusions: The use of equations to determine medication dosages presents considerable risk to patients for errant dosing and subsequent adverse events or therapeutic failure. Errors may occur in any component of a dosage equation." (*Arch. Pediatr. Adolesc. Med.* 1998 Apr.: 152 (4): 340–4, "Errors in the Use of Medication Dosage Equations.")

Further errors in medical dosage arise from the conversion of dosage units prescribed by the physician into pharmaceutical standard dosages. In cases where the prescriptive drugs are provided in solution at a specific concentration per volume of fluid, or a specific mass per tablet, a clinician must compute the correct total dosage to be administered to a patient. For example, most common problems in administering medications in healthcare are associated with conversions of drug dosage units.

Other errors in medicinal calculations occur with the administration of medication by intravenous fluids. Current methods for assuring accuracy in administering medications via intravenous fluids include programmable pumps similar to those pump's disclosed in U.S. Pat. Nos. 5,772,635; 5,681,285; 4,898,578; and 4,714,462. However, such programmable pumps are costly, expensive to maintain, and not always readily available. Therefore, manual hand calculations for administering medications using intravenous fluid are very often required. In such cases, intravenous fluids are administered by manually setting a drip chamber to allow a certain number of drops per minute to enter the intravenous tubing from the IV bag and to flow into the patient's vein. When the nurse or technician manually sets the flow rate by setting drip chambers, they have to carry out hand calculations to determine the appropriate number of drops per minute for the fluid to flow in accordance with the correct total dose for the patient. Since there are no quick and easy-to-use devices available to help perform such dosage conversions, hand calculations of drug dosages or flow rates are often performed.

Miscalculation of medication dosages can arise from incorrect manual calculations by the health care professional or student due to errors in calculation setups or in incorrect data entry. In particular, beginning nursing students and/or medical assistants encounter problems as they learn to correctly set up equations. Errors often arise from simple arithmetic mistakes in addition, subtraction, multiplication, and division. It has been noted that "medication error is a preventable event that may cause or lead to inappropriate medication use or patient harm while the medication is in the control of the health care professional, patient, or consumer. Such events may be related to professional practice; health care products, procedures, and systems including prescribing, order communication; product labeling, packaging and nomenclature; compounding, dispensing, distribution; administration; education; monitoring; and use." (*About Medication Errors*, National Coordinating Council for Medication Error Reporting and Prevention, 1998–1999.)

Several complex, hand-held apparatuses have been developed to assist healthcare professionals in evaluating medical information. For example, U.S. Pat. No. 6,167,412 teaches a hand-held calculator that performs specific clinical functions including storage/recall for numbers, phone directory, degree/radian, time, date alarms, and hemodynamics and cardiac functions; U.S. Pat. No. 5,630,664 discloses a hand-held apparatus for calculating and converting ECG waveforms and other graphically displayed data; and U.S. Pat. No. 5,915,971 teaches a hand-held device for teaching healthcare professionals how to determine a calculated drug dosage.

Further apparatuses directed to performing or recording medical information require a means for communicating with a host computer or server. For example, U.S. Pat. No. 5,781,442 discloses a system and method for patient care management; U.S. Pat. No. 5,272,318 teaches a system for ensuring proper treatment is being administered to the correct patient; U.S. Pat. No. 5,261,702 teaches a system for monitoring daily administration of medication to a patient; U.S. Pat. Nos. 5,088,981 and 4,810,243 disclose various programmable systems for customized delivery of medication to a patient; and U.S. Pat. No. 4,807,170 discloses a computer system for calculating drug administration rates for IV systems.

Although these various devices are beneficial in the health care profession, each is complex to operate and requires in-depth instruction on use. In addition, such devices are often expensive to purchase and to maintain. More importantly, these devices may actually lead to further dosage miscalculations as a result of user inability to properly operate the device.

Therefore, a quick and simple method and device for calculating dosage rates would benefit patient treatment, as current methods for determining drug dosages or flow rates are either manually/mentally calculated or require in-depth understanding of complex devices. Implementing a quick and simple means for accurately converting and calculating prescription dosages would also relieve clinicians from the time-consuming task of performing tedious and repetitive calculations and reduce the potential life threatening errors generated by hand calculations.

BRIEF SUMMARY

The subject invention provides a system and method for quick and easy calculation of medication dosages to overcome problems in current methods and systems for calculating dosages. The invention can be implemented in numerous ways, including as a system, a device, a method, or a computer readable medium. Several embodiments of the invention are discussed below. Specifically exemplified herein are embodiments for use in the healthcare industry. However, it is to be understood that the principles underlying the present invention may be applied in other applications.

As a computer system, an embodiment of the invention includes a database containing at least one of data, a display device and a processor unit. The display device has a plurality of display areas (windows). The processor unit operates to receive inputs, access the database to retrieve the data from the corresponding associated tables, perform calculations, and then display the results in the display areas.

As a device, the present invention may include at least one processor, a memory coupled to the processor, and a program (software) residing in the memory which implements the methods of the present invention. An embodiment of the invention provides a portable, handheld, battery-operated device having software to compute drug dosages. Alternatively, the software for computing drug dosages may be installed in personal assistant devices (PDAs) and similar computer-like devices. The device according to this invention provides standard input values for variables used in determining the correct amount of the prescribed drug to be administered. Limited key functions are included to provide a practical and user-friendly device for making quick calculations to administer drugs to patients. The keyboard in the system of the invention includes keys connected to a computation device installed with conversion software. The conversion software is preferably a program format enabling easy calculations and conversions of dosage units.

Identified variables provided by the device include: drug form and unit (tablets or capsules in milligrams, tablets in grains, liquids in milliliters), dosage per unit (milligrams per tablet or capsule, grains per tablet, milligrams per milliliter, units per milliliter), prescribed dosage, intravenous fluids, total milliliters per intravenous bag, hours to administer, milliliters per hour, embedded functions (60 milligrams per grain; 10 drops per milliliter; 15 drops per milliliter; 60 drops per milliliter). Most drugs are provided in a specific concentration either per volume of fluid or a specific weight per tablet or capsule.

The method of the invention for calculating and converting physician-prescribed drug dosage into standard pharmaceutical units includes the steps of: supplying to a device of the invention data indicative of the known form of medication to be administered, identifying and selecting the standard pharmaceutical unit to be calculated, supplying numerical data values of physician-prescribed variables to the device, and computing the previously selected standard pharmaceutical unit for administration to the patient. The method of the present invention may be implemented as a computer program product with a computer-readable medium having code thereon. The program product includes a program and a signal bearing media bearing the program.

An object of the present invention is to provide user-friendly devices for use by medical personnel and/or for training purposes for administration of various forms of drugs from stock supplies to accurately fill a physician's order.

Another object of the invention is to prevent or reduce setup errors, one of the most common areas of mistake in calculating medication dosages.

A further object of the invention is to provide simplicity of calculations and an easy-to-use interface between the user and a device according to the invention.

Another object is to provide a simple and cost-effective device.

Yet another object of the invention is to ease clinician workload and mental strain induced in emergent situations, and reduce errors due to faulty medical calculations.

DETAILED DISCLOSURE

The present invention provides an accurate and simple medication dosage calculating system. The invention provides nurses as well as other healthcare professionals a means for rapid and accurate calculations pertaining to the administration of drugs prescribed by a physician. Medication dosages in various forms, including tablet/capsule, liquid, or vial forms as well as intravenous administration of fluids to a patient can be calculated and converted. One advantage of the present invention is the provision of a handheld, battery-operated calculating device for performing drug dosage calculations in a simple, straightforward manner. The calculating/conversion device according to the invention allows simple methods of determining the correct amount of the drug to be administered to a patient by providing value-input keys for relevant variables, coupled with logical sequencing of data entry using these variable keys.

In a preferred embodiment of the present invention, the calculating device has a value-input keypad consisting of approximately twenty keys to enable user input of medication values. The keys represent standard variables and units frequently and routinely used in determining the correct amount of a medication to be administered. In a preferred embodiment, these variables are conveniently arranged so that they are divided into different columns on the casing of the device; each column representing a category of variables with similar function. Additionally, the calculating device also embodies a conventional numeric calculator keypad with basic arithmetic functions below the value-input keypad.

For purposes of illustration, in the following discussion one particular application and embodiment of the present invention is described. The following figures are intended only to illustrate the possible modes of operation of the device of the present invention; however, the indicated figures are not to be construed as limiting the scope of the invention.

Figure 1:
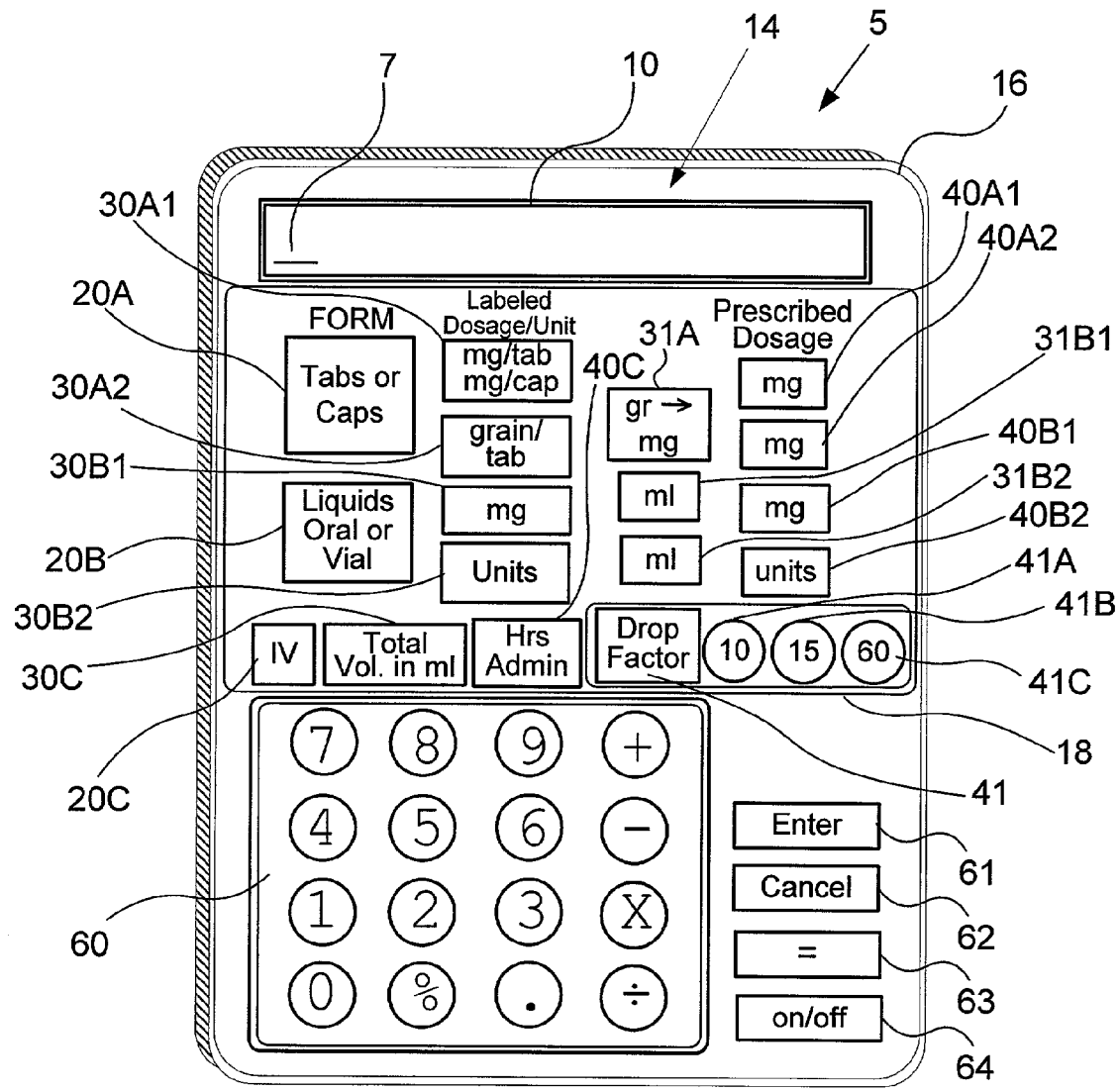
FIG. 1 is a front view of the hand-held device representing an embodiment of the present invention in the activated mode.

Referring now to FIG. 1, a front view of the handheld, drug dosage calculating device 5 according to the invention is shown. The device 5 is comprised of a multi-character, liquid crystal display (LCD) output screen 10 and a keyboard 14 mounted in a casing 16. The keyboard 14 and the screen 10 are connected to a computation system, which receives inputted data, computes the necessary calculation and conversion, and produces as output a number figure of the appropriate dosage of a drug to be administered to the patient on the display screen 10. The calculating device also has a power supply that supplies power to the calculating device 5, preferably implemented as one or more batteries (not shown) to enhance the portability of the device 5.

In one embodiment, the keyboard 14 comprises two major components: 1) user operable medication value-input keypad 18 for primary variables and units that are considered in calculating dosage of a drug administered to a patient; and 2) a conventional calculator keypad 60 consisting of basic numeric digit keys of 0–9, a percentile key, and a decimal point key; and arithmetic function keys including an equal sign key 63, a cancel key 62, an enter key 61, and an ON/OFF key 64 to allow a user to activate the device 5 and perform necessary numeric computations. In one embodiment, the device 5 is programmed so that it can operate in either simple calculator mode or medical dosage conversion mode.

In a preferred embodiment, the user operable medication value-input keypad 18 of the keyboard 14 of the device 5 represents various primary variable function keys used in performing drug dosage calculations. The function of these various keys will be described in greater detail below in conjunction with the accompanying drawings and references to those drawings.

A first column, labeled as FORM, of the value-input keypad 18, represents a set of keys for selecting one of three different forms in which medications are usually available, namely tablets or capsules, oral or vial liquids, and intravenous fluids. Any given medication or drug will routinely be administered to a patient in one of these three forms, or in the units of Tablets or Capsules 20A, Liquids 20B or IV Fluids 20C.

A second column, labeled as LABELED DOSAGE PER UNIT, representing standard dosage per unit of a drug as supplied by a pharmacy, includes keys for milligrams per tablet or capsule 30A1 and grains per tablet 30A2, which has immediately next to it a separate embedded function key that directly converts grains into milligrams 31A (labeled as gr→mg) to be used in conjunction with the Tab or Capsule key 30A2 described above. Additional unit keys to be used in conjunction with the Liquids key 20B include oral liquids milligram key 30B1 and oral liquids milliliter key 31B1 placed side by side; and vial units key 30B2 and vial milliliter key 31B2 placed side by side. Under this column, the key for standard dosage per unit of intravenous fluid is labeled as Total Volume in ml 30C.

A third column, labeled as PRESCRIBED DOSAGE, representing the dosage of a drug prescribed by the physician, includes three separate milligram (mg) keys 40A1, 40A2, and 40B1, and one units key 40B2. The first two mg keys 40A1 and 40A2 are used in conjunction with Tabs or Caps key 20A, the third mg key 40B1 is to be used in conjunction with Liquids key 20B along with vial units key 40B2. This column also includes a separate functional key as a prescribed dosage to be used for IV Fluids, labeled as Hrs to Administer 40C.

As described above, the intravenous category, with IV Fluid key 20C placed in the first column, would use as its variables: the total milliliters per bag of the IV fluid key 30C placed in the second column; the number of hours to administer the fluid key 40C grouped together with the keys that are in the third column under PRESCRIBED DOSAGE. For intravenous fluids, unlike the other medications that come in liquids or tablets or capsule, the number of drops of IV fluids must be configured along with the duration of the IV fluids of prescribed dosage to be administered. Therefore, along with the Hrs to Administer key 40C, a key for determining the number of drops per milliliter is provided labeled as Drop Factor 41, and are placed in a fourth column. A user will press this key and then enter in any of the already configured drops per milliliter keys, which are numbered 10, 15, and 60 from top to bottom, illustrated as 41A, 41B, and 41C, respectively.

The calculator keypad 60 is used to enter the data to a computation system that computes the unknown quantity. A display screen 10 on the device 5 of the present invention displays calculated amounts as the data is entered. The simplicity of the device coupled with logical sequencing of data entry makes this invention unique and useful.

FIG. 1 also illustrates an initial view of display screen 10 when the device 5 is turned on by pressing the ON/OFF key 64. In a preferred embodiment, the display screen 10 exhibits a blinking cursor 7 as soon as the device 5 is turned on, to let the user know that the device 5 is ready to receive data. Once the device 5 is ready for use, the user may operate the calculating device 5 by performing the following general sequence of steps:

Selecting a FORM key;
Selecting a LABELED DOSAGE/UNIT key;
Entering numerical values of the pharmaceutical standard dosage per unit using the calculator keypad 60;
Pressing the ENTER key 61;
Selecting a PRESCRIBED DOSAGE key;
Entering numerical values of the physician prescribed dosage using the calculator keypad 60; and
Pressing the ENTER key 61.

As soon as the ENTER key 61 is depressed the second time, the display screen 10 will show: "Administer X tabs or caps," X representing the correct number of tabs or capsules to be administered to the patient. As illustrated by FIG. 1 and the above-described logical sequencing of data entry, the key feature of the present invention is the simple and logical sequence of steps required to perform the drug dosage conversion.

FIGS. 2–5 further illustrate the basic drug dosage conversion interface between the user and the device 5 of the present invention with specific examples from each different form of drugs with various visual outputs shown on the display screen 10 of the device of FIG. 1. These illustrations should not be construed as limiting. These illustrations also apply to the alternative form/method of practicing the invention by means of using the programmable devices implemented on person digital assistants (PDAs) or computer-like computational devices.

Figure 2:
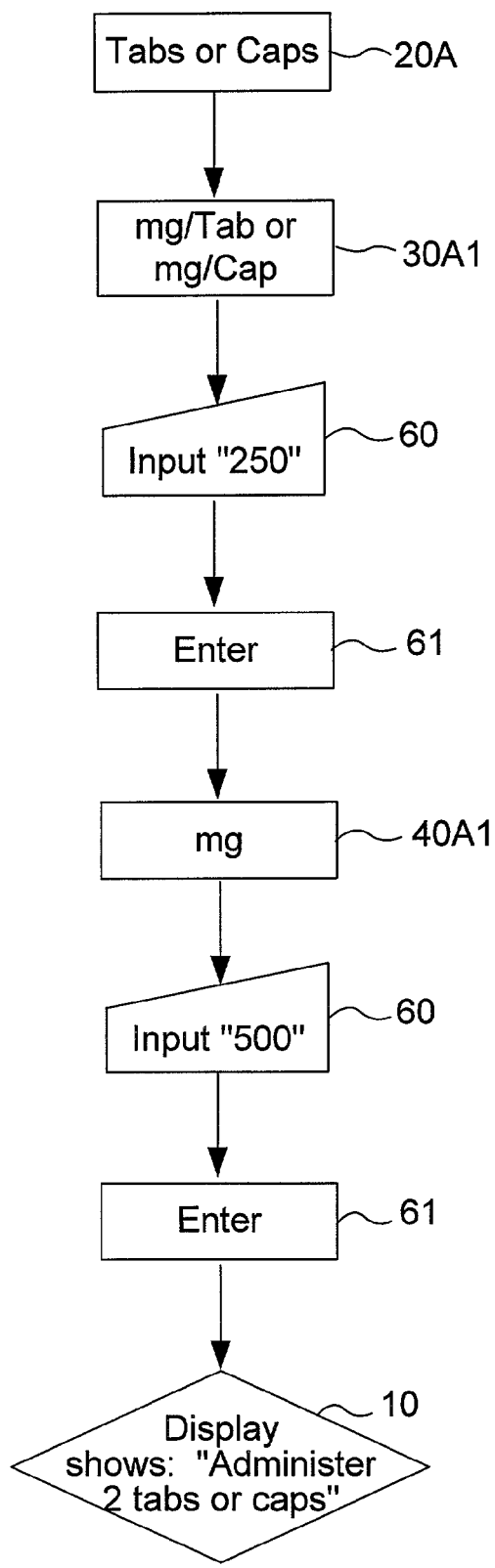
FIG. 2 is a flow diagram illustrating the operational flow process used for performing a representative dosage conversion from physician-prescribed milligrams to pharmaceutical standard milligrams per tablet (or capsule).

Referring to FIG. 2 for further detailed illustration of the operational scheme of the device 5, the calculation and/or conversion procedure for practicing the invention is shown for all medications that are to be administered in the forms of tablets or capsules. FIG. 2 specifically illustrates the sequence of steps that a user performs to arrive at the desired drug dosage for the medication Erythromycin 500 mg po qd to be administered to a patient when Erythromycin is supplied (labeled dosage) in 250 mg per tablet. The medication Erythromycin 500 mg po qd is used herein only as an example of an amount and type of drug prescribed by a physician. FIG. 2 illustrates the following general sequence of steps to operate the calculating device 5:

Pressing the Tablets or Capsules 20A key;
Pressing the milligrams per tablet or capsule 30A1 key;
Entering numerical value "250" (the pharmaceutical standard dosage per unit) using the calculator keypad 60;
Pressing the ENTER key 61;
Pressing the prescribed milligram dosage key 40A1;
Entering numerical value "500" (as indicated above for Erythromycin 500 mg) using the calculator keypad 60; and
Pressing the ENTER key 61; to command the device to convert and calculate the necessary medication to be administered to the patient. In this particular example, the display screen 10 will show: "Administer 2 tabs or caps."

Figure 3:
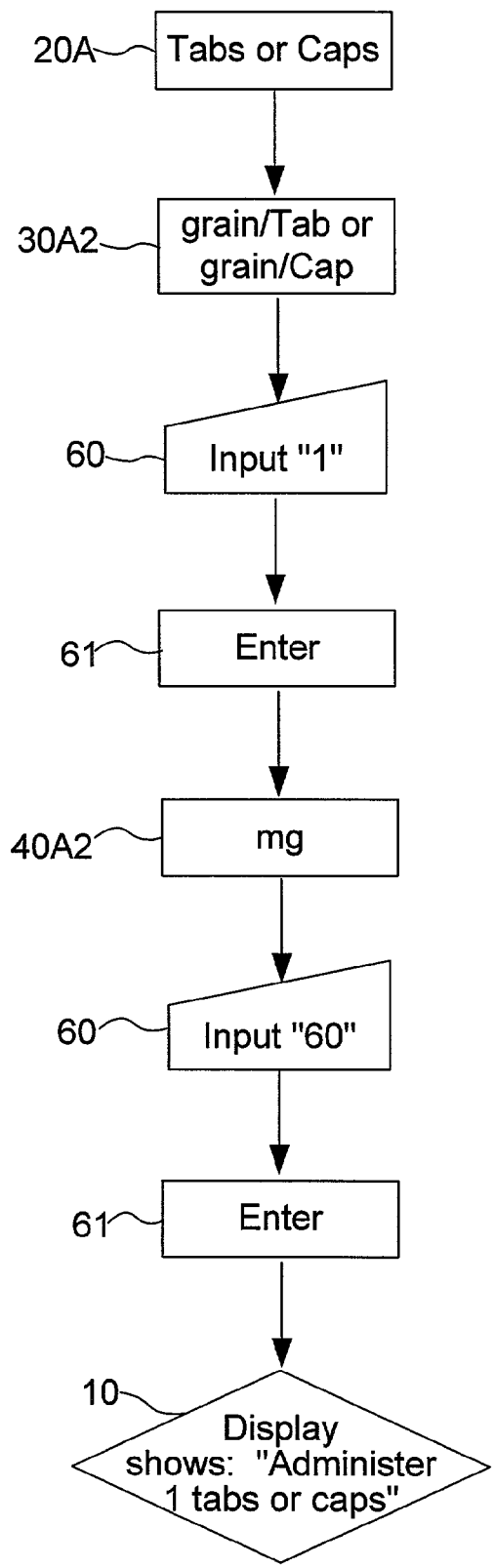
FIG. 3 is a flow diagram illustrating the operational flow process used for performing a representative dosage conversion from physician-prescribed milligrams to pharmaceutical standard grains per tablet (or capsule).

Referring to FIG. 3, which illustrates the operational steps of performing drug dosage conversion in the unit of grain rather than in mg as was the case in FIG. 2. FIG. 3 specifically illustrates the sequence of steps that a user performs to arrive at the desired drug dosage for the medication Thyroid 60 mg po qd as prescribed by a physician when Tyroid is supplied (labeled dosage) in 60 mg (1 grain) per tablet. The medication Thyroid 60 mg po qd is used herein only as an example of an amount and type of drug to be administered to a patient. FIG. 3 illustrates the following general sequence of steps to operate the calculating device 5:

Pressing the Tablets or Capsules 20A key;
Pressing the grains per tablet 32A2 key;
Entering numerical value "1" (the pharmaceutical standard dosage per unit) using the calculator keypad 60;
Pressing the ENTER key 61;
Pressing the prescribed milligram dosage key 40A2;
Entering numerical value "60" (as indicated above for Thyroid 60 mg) using the calculator keypad 60; and
Pressing the ENTER key 61; to command the device to convert and calculate the necessary medication to be administered to the patient. In this particular example, the display screen 10 will show: "Administer 1 tabs or caps."

Figure 4:
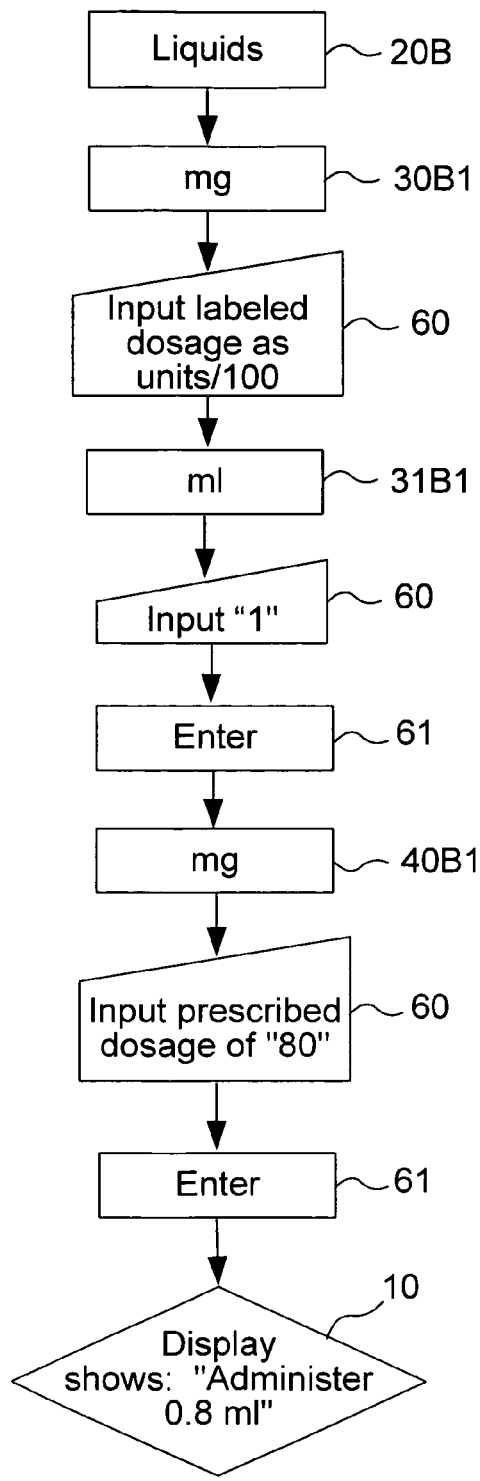
FIG. 4 is a flow diagram illustrating the operational flow process used for performing a representative dosage conversion of the liquid form of drugs.

FIG. 4 illustrates the operational steps of performing dosage conversion of drugs in liquid forms. FIG. 4 specifically illustrates the sequence of steps that a user performs to arrive at the desired drug dosage for the medication Demerol 80 mg IM q3-4h as prescribed by a physician when Demerol I supplied (labeled soage) at 100 mg per ml. The medication Demerol 80 mg IM q3-4h is used herein only as an example of an amount and type of drug to be administered to a patient. FIG. 4 illustrates the following general sequence of steps to operate the calculating device 5:

Pressing the Liquids 20B key;
Pressing the milligram (mg) 30B1 key;
Entering numerical value "100" (the pharmaceutical standard dosage per unit) using the calculator keypad 60;
Pressing milliliter (ml) 31B1 key;
Entering numerical value "1" using the calculator keypad 60;
Pressing the ENTER key 61;
Pressing the prescribed milligram dosage key 40B1;
Entering numerical value "80" (as indicated above for Demerol 80 mg) using the calculator keypad 60; and
Pressing the ENTER key 61; to command the device to convert and calculate the necessary medication to be administered to the patient. In this particular example, the display screen 10 will show: "Administer 0.8 ml."

Figure 5:
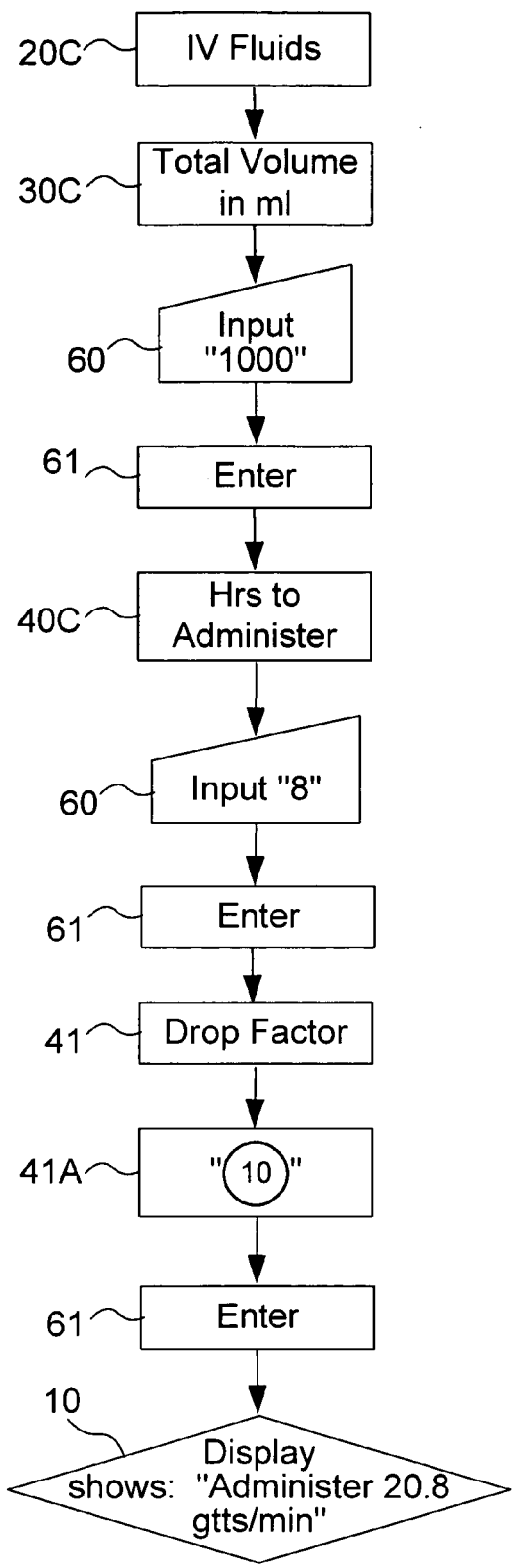
FIG. 5 is a flow diagram illustrating the operational flow process used for performing a representative dosage conversion of intravenous fluids.

FIG. 5 illustrates the operational steps of performing dosage conversion of IV Fluids. FIG. 5 specifically illustrates the sequence of steps that a user performs to arrive at the desired medication prescription for 1000 ml D5W q8h, available IV tubing drop factor of 10. The medication 1000 ml D5W q8h and IV tubing drop factor of 10 is used herein only as an example. FIG. 5 illustrates the following general sequences of steps to operate the calculating device 5:

Pressing the IV Fluids 20C key;
Pressing the Total Volume in ml 30C key;
Entering numerical value "1000" (as prescribed by the physician) using the calculator keypad 60;
Pressing the ENTER key 61;
Pressing the Hrs to Administer 40C key;
Entering numerical value "8" (as indicated above as q8h) using the calculator keypad 60;
Pressing the ENTER key 61;
Pressing the Drop Factor 41 key;
Pressing drop factor 10 key 41A; and
Pressing the ENTER key 61; to command the device to convert and calculate the necessary medication to be administered to the patient. In this particular example, the display screen 10 will show: "Administer 20.8 gtts/min."

The keys of the device of the subject invention can be color-coded to facilitate accurate and easy identification of the desired keys. Thus, for example, all of the keys having relevance to a particular dosage form may be the same color.

Based on the foregoing specification, the invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

One skilled in the art of computer science will easily be able to combine the software created as described with appropriate general purpose or special purpose computer hardware to create a computer system or computer subsystem embodying the method of the invention. An apparatus for making, using or selling the invention may be one or more processing systems including, but not limited to, a central processing unit (CPU), memory, storage devices, communication links and devices, servers, I/O devices, or any sub-components of one or more processing systems, including software, firmware, hardware or any combination or subset thereof, which embody the invention. User input may be received from the keyboard, mouse, pen, voice, touch screen, or any other means by which a human can input data into a computer, including through other programs such as application programs.

It should be understood that the examples and embodiments described herein are for illustrative purposes only and that various modifications or changes in light thereof will be suggested to a person skilled in the art and are to be included within the spirit and purview of this application and the scope of the appended claims.

I claim:

1. A medication dosage conversion device for easily and accurately determining the amount of medication to be administered to a patient based upon a prescribed dosage which is in different units from the units in which the medication is supplied; wherein said device comprises:
   a) a first means for entering a form of medication;
   b) a second means for entering a unit of dosage of a medication as supplied; and
   c) a third means for entering a prescribed dosage of the medication;
   d) computation means for converting the input data into information regarding the amount of the medication to administer to the patient; and
   e) a display screen;
wherein said device converts the input data into output information providing the amount of medication to deliver, and wherein said output information is shown on said display screen.

2. The device, according to claim 1, wherein said device is portable.

3. The device, according to claim 2, wherein said device is handheld.

4. The device, according to claim 1, which is mounted at a nurse's station or in a patient's room.

5. The device, according to claim 1, wherein said input means is are selected from the group consisting of touch screens, voice recognition, and keypads.

6. The device, according to claim 1, wherein said display screen comprises a liquid crystal display.

7. The device, according to claim 1, wherein said computation means computes dosage amounts for at least two dosage forms of medication.

8. The device, according to claim 7, wherein the dosage forms include solid and liquid dosage forms.

9. The device, according to claim 1, wherein said display screen displays numbers and letters corresponding to input data and output information.

10. The device, according to claim 1, wherein said means for entering input data comprises:
    a) a first set of keys for entering a form of medication;
    b) a second set of keys for entering a unit of dosage of a medication as supplied; and
    c) a third set of keys for entering a prescribed dosage of the medication.

11. The device, according to claim 10, wherein said first set of keys comprises keys for selecting one of the following:
    a) tablets or capsules;
    b) orally-consumed liquids; and
    c) intravenous fluids.

12. The device, according to claim 10, wherein said second set of keys comprises at least two of the group consisting of:
    a) a mg/tablet or mg/capsule key;
    b) a grain/tab key;
    c) a grain to mg converter key;
    a) an oral liquids mg key;
    b) an oral liquids ml key;
    c) a vial units key;
    d) a vial ml key; and
    e) a total volume in ml key.

13. The device, according to claim 10, wherein said third set of keys comprises at least two of the following:
    a) a mg key;
    b) a units key;
    c) an hours to administer key; and
    d) a drop factor key.

14. The device, according to claim 13, wherein said device comprises keys with an embedded function for automatically providing the number of drops to be administered for intravenous administration.

15. The device, according to claim 14, with keys corresponding to 10, 15 and 60 drops.

16. The device, according to claim 1, wherein said calculator keypad further performs numeric computations.

17. The device, according to claim 1, wherein said computation means comprises software for converting said input data to said output information.

18. A method for easily and accurately determining the amount of medication to be administered to a patient based upon a prescribed dosage which is in different units from the units in which the medication is supplied; wherein said method comprises:
    a) receiving first input data indicative of the known form of medication to be administered,
    b) receiving second input data indicative of the standard pharmaceutical unit in which the dosage is to be expressed,
    c) receiving third input data values of physician-prescribed variables,
    d) computing the dosage for administration to the patient as expressed in the previously selected standard pharmaceutical unit, and
    e) displaying the amount of medication to be administered to the patient;
    wherein said input data is received in steps (a)–(c) by:
        i) a first means for entering a form of medication;
        ii) a second means for entering a unit of dosage of a medication as supplied; and
        iii) a third means for entering a prescribed dosage of the medication, respectively.

19. The method, according to claim 18, wherein said input data is received in steps (a)–(c) by an input means selected from the group consisting of touch screens, voice recognition, and keypads.

20. The method, according to claim 18, wherein the step of displaying the amount of medication comprises displaying said amount on a liquid crystal display.

21. The method, according to claim 18, wherein step (d) further comprises computing dosage amounts for at least two dosage forms of medication.

22. The method, according to claim 21, wherein said step of computing dosage amounts comprises computing the dosage forms include solid and liquid dosage forms.

23. The method, according to claim 18, wherein said input data is received in steps (a)–(c) by:
    a) a first set of keys for entering a form of medication;
    b) a second set of keys for entering a unit of dosage of a medication as supplied; and
    c) a third set of keys for entering a prescribed dosage of the medication, respectively.

24. The method, according to claim 23, wherein said first set of keys comprises keys for selecting one of the following:
    a) tablets or capsules;
    b) orally-consumed liquids; and
    c) intravenous fluids.

25. The method, according to claim 23, wherein said second set of keys comprises at least two of the group consisting of:
- a) a mg/tablet or mg/capsule key;
- b) a grain/tab key;
- c) a grain to mg converter key;
- f) an oral liquids mg key;
- g) an oral liquids ml key;
- h) a vial units key;
- i) a vial ml key; and
- j) a total volume in ml key.

26. The method, according to claim 18, further comprising receiving input data via keys corresponding to 10, 15 and 60 drops.

27. The method, according to claim 18, further comprising performing additional numeric computation via a calculator keypad.

* * * * *